(12) United States Patent
Ljunggreen et al.

(10) Patent No.: US 6,287,283 B1
(45) Date of Patent: Sep. 11, 2001

(54) APPARATUS FOR THE REGISTRATION OF THE SETTING OF A MEDICAL DEVICE

(75) Inventors: Henrik Ljunggreen, Ballerup; Jens Munk, Stenløse; Lars Hofmann Christensen, Frederiksberg; Jens-Ulrik Poulsen, Virum; Jens Møller-Jensen, Copenhagen; Peter Møller-Jensen, Hørsholm, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/113,040

(22) Filed: Jul. 9, 1998

Related U.S. Application Data

(63) Continuation of application No. PCT/DK98/00188, filed on May 14, 1998.
(60) Provisional application No. 60/053,182, filed on Jul. 18, 1997.

(30) Foreign Application Priority Data

Jul. 11, 1997 (DK) .................................................. 0852/97

(51) Int. Cl.$^7$ .................................................. A61M 5/00
(52) U.S. Cl. .......................... 604/207; 604/208; 604/211; 604/198; 128/919
(58) Field of Search .................................... 604/131, 181, 604/186, 207, 151, 189, 208, 211, 192, 198, 263, 197, 209, 241–243, 246; 128/919

(56) References Cited

U.S. PATENT DOCUMENTS

| | | | |
|---|---|---|---|
| 4,592,745 | * | 6/1986 | Rex et al. . |
| 4,636,201 | * | 1/1987 | Ambrose et al. . |
| 4,883,472 | * | 11/1989 | Michel . |
| 4,959,056 | * | 9/1990 | Dombrowski et al. . |
| 4,973,318 | * | 11/1990 | Holm et al. ............................ 604/208 |
| 5,002,536 | * | 3/1991 | Thompson et al. . |
| 5,009,640 | * | 4/1991 | Pyret et al. . |
| 5,017,190 | * | 5/1991 | Simon et al. . |
| 5,098,400 | * | 3/1992 | Crouse et al. . |
| 5,279,586 | * | 1/1994 | Balkwill .............................. 604/207 |
| 5,494,036 | * | 2/1996 | Uber, III et al. .................... 128/655 |
| 5,509,905 | * | 4/1996 | Michel ................................ 604/207 |
| 5,522,799 | * | 6/1996 | Furukawa .............................. 604/65 |
| 5,536,249 | * | 7/1996 | Castellano et al. .................... 604/65 |
| 5,573,506 | * | 11/1996 | Vasko ................................... 604/65 |
| 5,593,390 | * | 1/1997 | Castellano et al. ................. 604/187 |
| 5,690,618 | * | 11/1997 | Smith et al. ......................... 604/232 |
| 5,704,922 | * | 1/1998 | Brown ................................. 604/207 |
| 5,725,508 | * | 3/1998 | Chanoch et al. .................... 604/207 |
| 5,728,074 | * | 3/1998 | Castellano et al. ................. 604/207 |
| 5,782,814 | * | 7/1998 | Brown et al. ....................... 604/207 |
| 5,795,333 | * | 8/1998 | Reilly et al. ........................ 604/154 |
| 5,807,336 | * | 9/1998 | Russo et al. ........................ 604/131 |
| 5,843,047 | * | 12/1998 | Pyrozyk et al. . |
| 5,873,856 | * | 2/1999 | Hjertman et al. . |
| 5,947,934 | * | 9/1999 | Hansen et al. . |

FOREIGN PATENT DOCUMENTS 0 635 277    1/1995   (EP) .

* cited by examiner

Primary Examiner—Richard K. Seidel
Assistant Examiner—LoAn H. Thanh
(74) Attorney, Agent, or Firm—Skadden, Arps, Slate, Meagher & Flom LLP

(57) ABSTRACT

The invention concerns an apparatus for the registration of the setting of a medical device, the setting of which implies a mechanical adjustment of at least two relatively moveable elements of the device. The invention is characterized in that the apparatus is intended for disconnectible engagement with the medical device, and that it has detector means for detecting the mechanical adjustment and has information means arranged for providing information related to said mechanical adjustment.

22 Claims, 7 Drawing Sheets

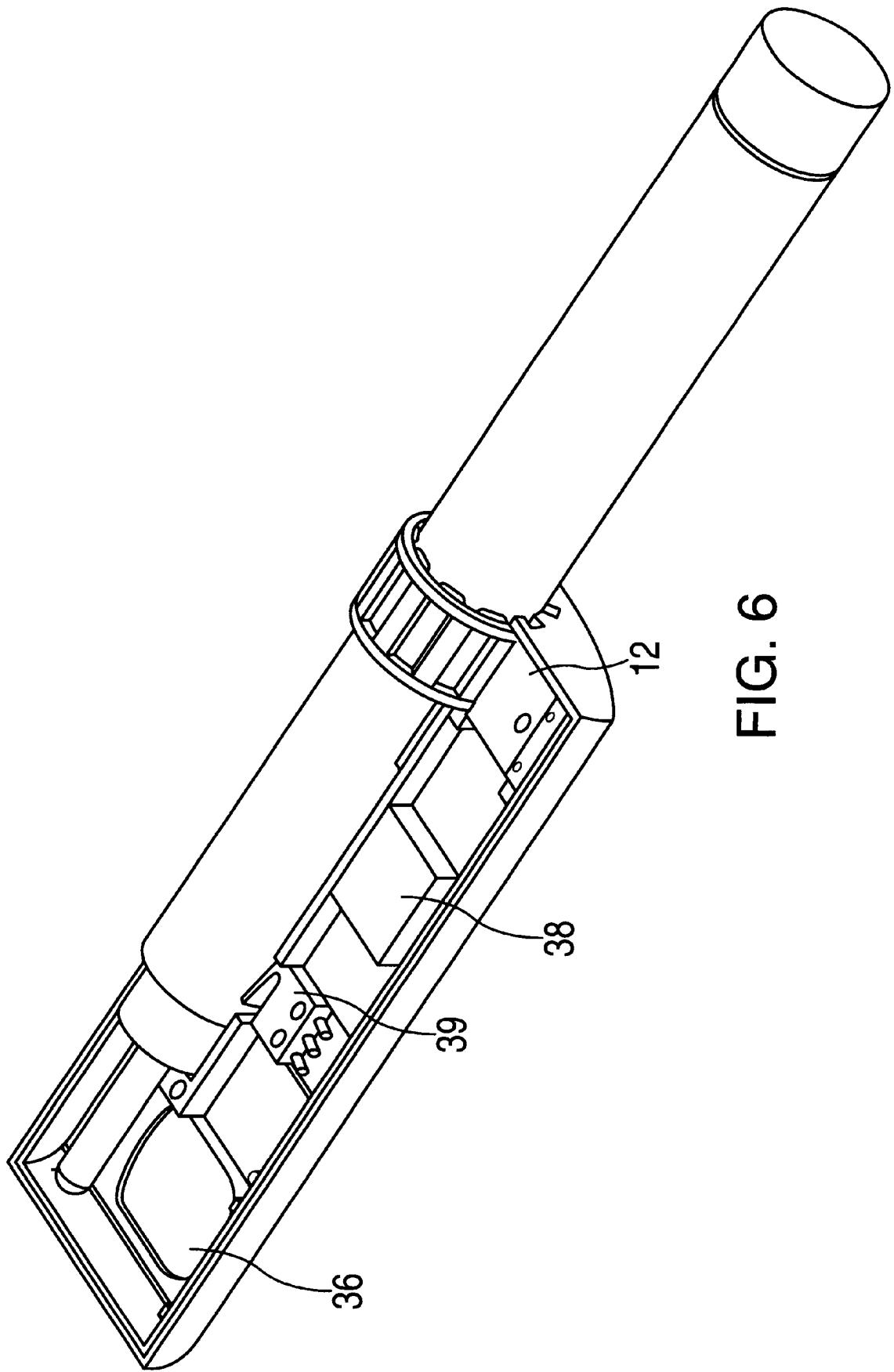

Figure 1:
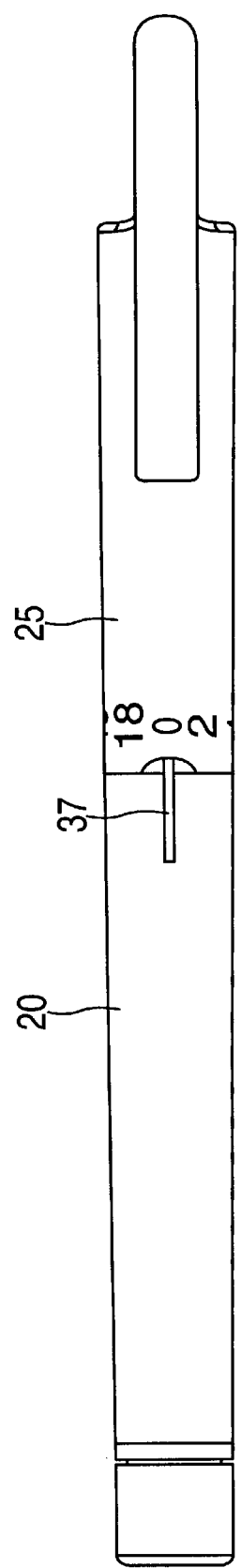

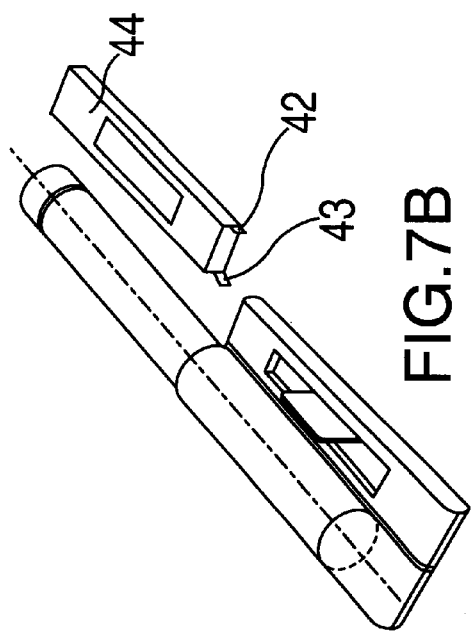
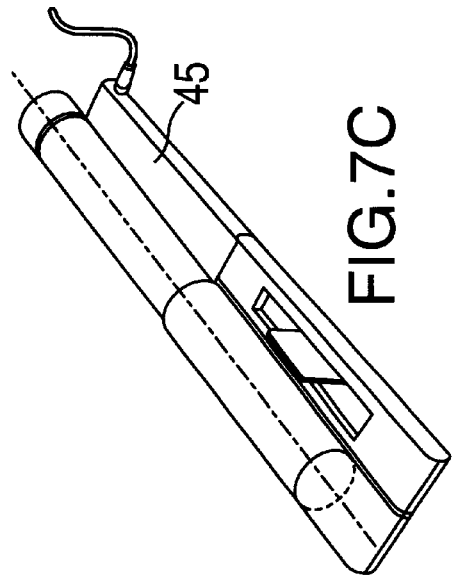
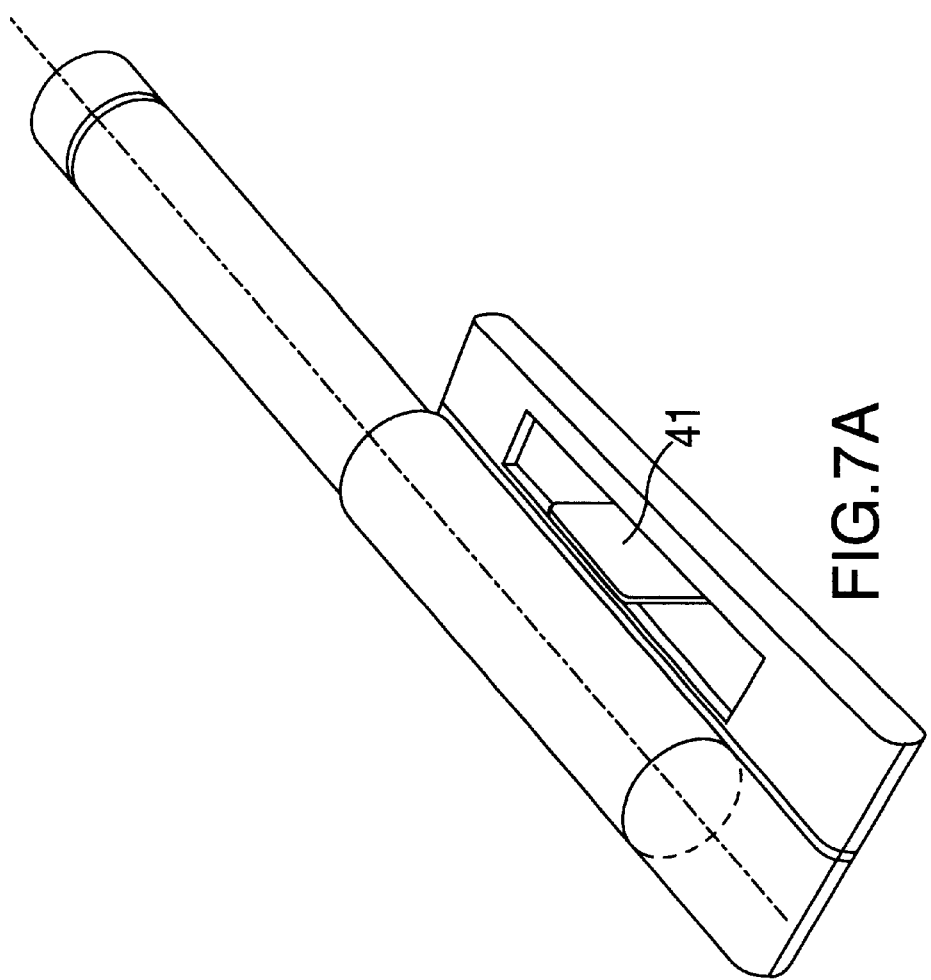

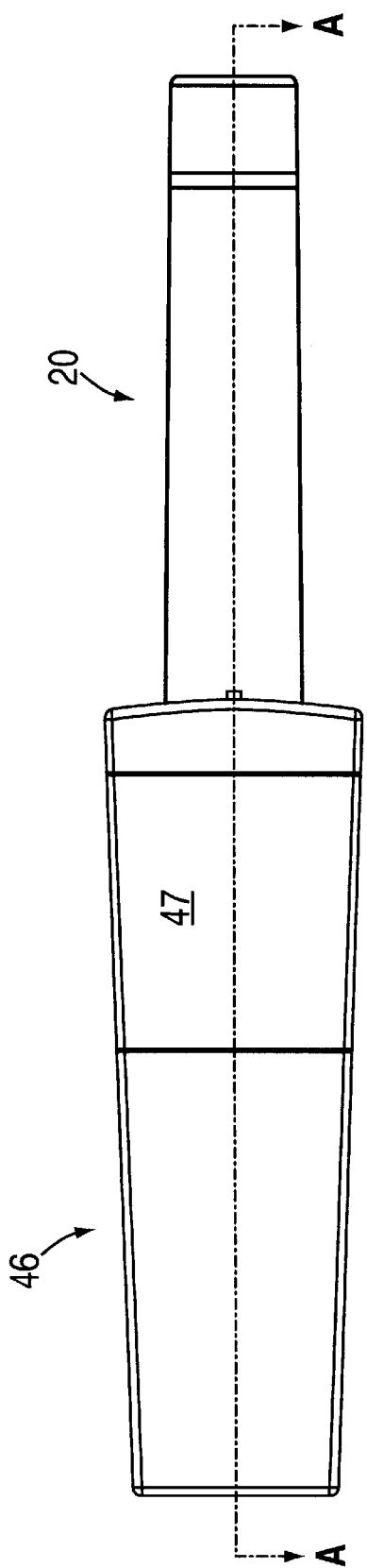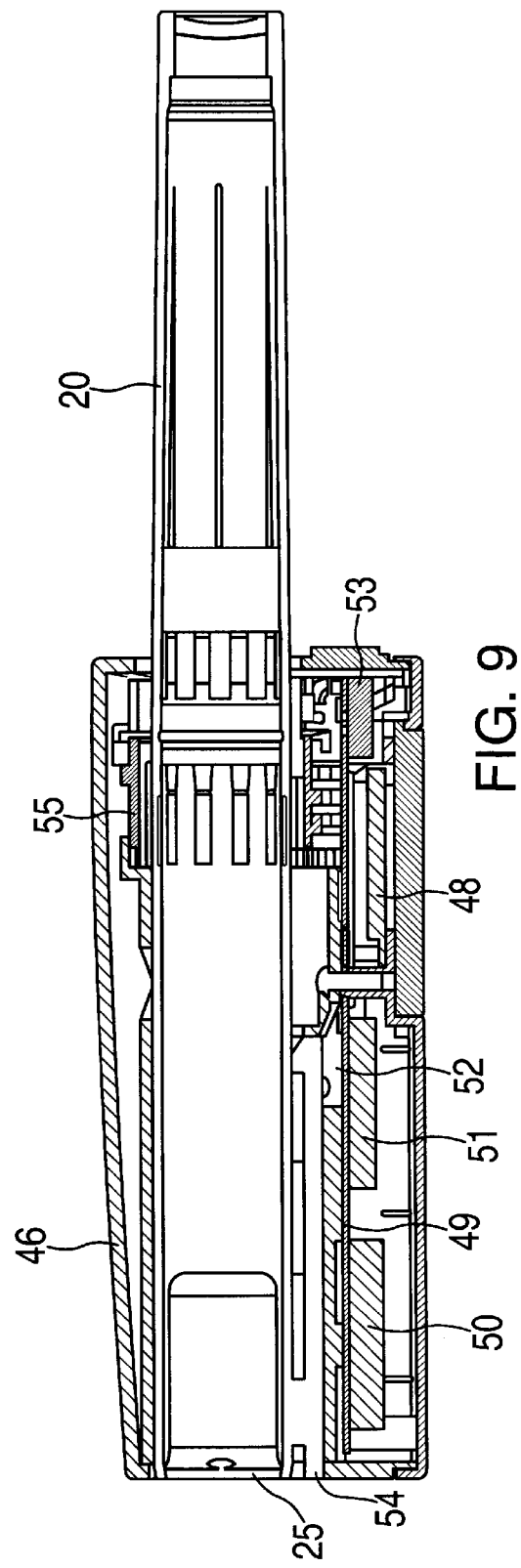
FIG. 8
FIG. 9

APPARATUS FOR THE REGISTRATION OF THE SETTING OF A MEDICAL DEVICE

CROSS-REFERENCE TO RELATED APPLICATIONS

This application claims priority under 35 U.S.C. 119 of Danish application 0852/97 filed on Jul. 11, 1997, and of U.S. provisional application Ser. No. 60/053,182 filed on Jul. 18, 1997. This application is a continuation of International Patent Application serial no. PCT/DK98/00188 filed on May 14, 1998 via PCT, the contents of which are fully incorporated herein by reference.

The invention relates to an apparatus for the registration of the setting of a medical device e.g. for indicating the dosages of pharmaceutical to be released from an adjustable dosage unit.

Especially within the medical field many devices are used of the type where an adjustment should be set during handling of the device and where data retrieval related to the setting is increasingly needed because the use of equipment for handling and displaying data has exploded.

In the following the invention will be explained in relation to a known device in the form of an adjustable dosage unit for the release of a dose of pharmaceutical.

Preferably such a dosage unit comprises a cylindrical casing for the dose of pharmaceutical, preferably insulin. The dosage unit is preferably of the type described in EP 327 910. When used for dosing suitable quantities of insulin, the cartridge for inserting in the dosage unit usually contains 1.5 ml. The insulin is of a concentration of e.g. 100 insulin units per ml whereby the cartridge contains 150 insulin units. When using the dosage unit, a pre-determined quantity is to be delivered per injection, preferably up to 40 insulin units.

Therefore, the dosage unit can be used for several injections per cartridge. The latter procedure requires a very accurate adjustment of the dosage to be injected per injection.

The dosage unit according to EP 327 910 is a very compact pen-like device which can easily be pre-adjusted to the desired dosing quantity by revolving the pen in relation to an end cap thereof. The desired dosing quantity is read by means of a suitable measuring scale.

However, it has been, realised that children or elderly persons, especially visually impaired persons, may encounter problems when reading the measuring scale which is divided into a scale for "ones" and one for "tens". Especially the scale of "tens" might be misinterpreted.

The object of the invention is to provide an apparatus allowing a more safe detecting of the setting of the medical device.

A further object of the invention is to provide a more safe reading of the pharmaceutical dosage given from a dosage unit.

A further object is to provide an apparatus which can be used in combination with existing dosage units e.g. of the type described in EP 327 910 for providing further information related to the dosage of pharmaceutical.

A further object is to provide for an apparatus which also allows for adopting the cap of an existing dosage unit.

These objects are accomplished by an apparatus which is intended for disconnectible engagement with the medical device, said apparatus having detector means for detecting the selected setting and information means for providing information related to said mechanical adjustment.

Preferably, the device may be a dosage unit having a pair of mutually movable elements for co-operating with respective elements in the apparatus. These elements could be mutually longitudinally displaceable but a very expedient embodiment comprises mutually revolving engagement elements of a kind also to be found on the unit known from EP 327 910. Thereby, the consumer does not need to buy a new and expensive injection unit. The apparatus according to the invention can be used as an add-on for the known pen-like injector already covering a major part of the world market.

When arranging the apparatus so that it can receive the first end of the dosage unit, whereby the adjustment of the dosage quantity is effected by revolving of the dosage unit relatively to the apparatus, the apparatus according to the invention will function just like the removable cap of the well-known insulin pen whereby the users will feel comfortable when using the new apparatus with their own and well-known insulin pen.

In a preferred embodiment the apparatus is arranged also to accommodate a removable cap of a well-known insulin pen whereby insulin which may leak from the needle will be picked up by the cap so that the insulin is prevented from causing bad smell or damaging the electronics in the apparatus according to the invention.

The apparatus according to the invention can be based on a purely mechanical or electromechanical basis. Even a purely mechanical device will enhance the safety in handling the insulin injector in that the apparatus can comprise rotating discs driven by the cooperating engagement elements, thereby making a very easily readable indication of the pre-selected dosage. Also pads with Braille can be incorporated in the apparatus.

Preferably, the detector means of the apparatus comprises a transducer for generating an electrical signal which represents the adjusted dosage quantity. The transducer is preferably arranged for providing different types of electrical signals when the dosage unit and the apparatus are turned relative to each other in one direction or in the opposite direction, respectively. Thereby it is easier to program an electronic programming unit in the apparatus.

The safety and versatile use of the apparatus can be further enhanced by incorporating an encoder in the transducer.

The information means preferably comprises a display unit which is controlled relative to the electrical signals from the transducer. Also a memory and programming unit as well as clock and timer means can be incorporated in the information means.

Preferably the apparatus is arranged to work with further add-on's, i.e. a sound module, a PC-link module, or a module for infrared transmission of information. These features can also be incorporated in the apparatus itself but when divided up in a number of add-on's, the user need not buy more than necessary.

In the following the invention will be described in more details in connection with an insulin injection unit but it will be understood that supervision of dispensing of other types of pharmaceutical can also be carried out by means of the apparatus according to the invention. E.g. an embodiment for cooperating with a dosage unit for pills is also within the scope of the invention.

Figure 2:
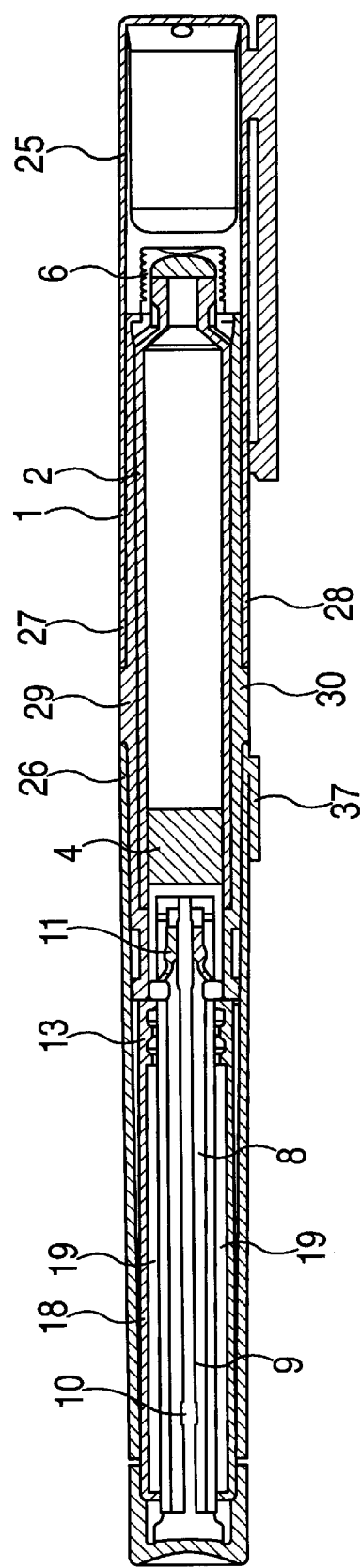
Figure 3:
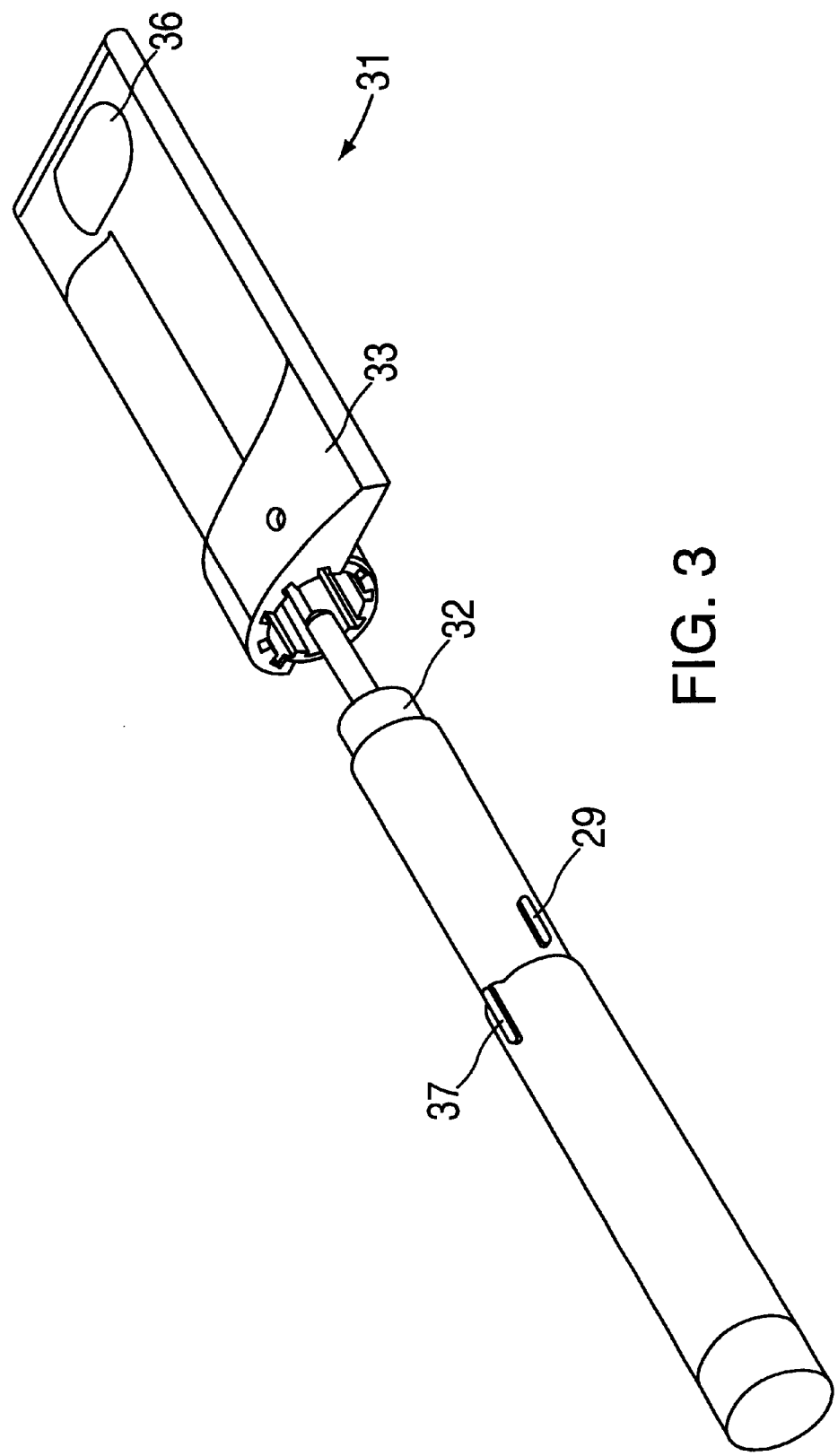
Figure 4:
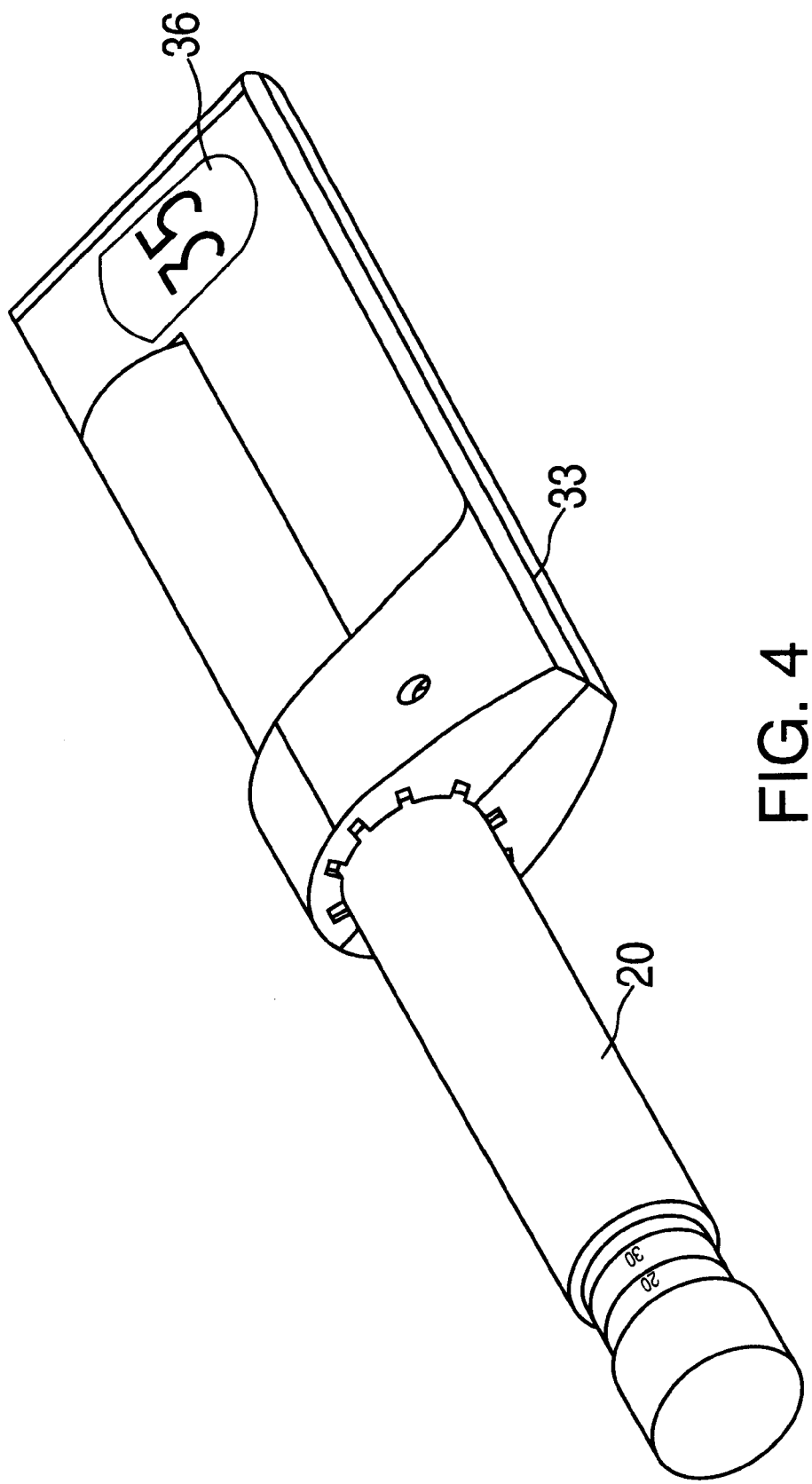
Figure 5:
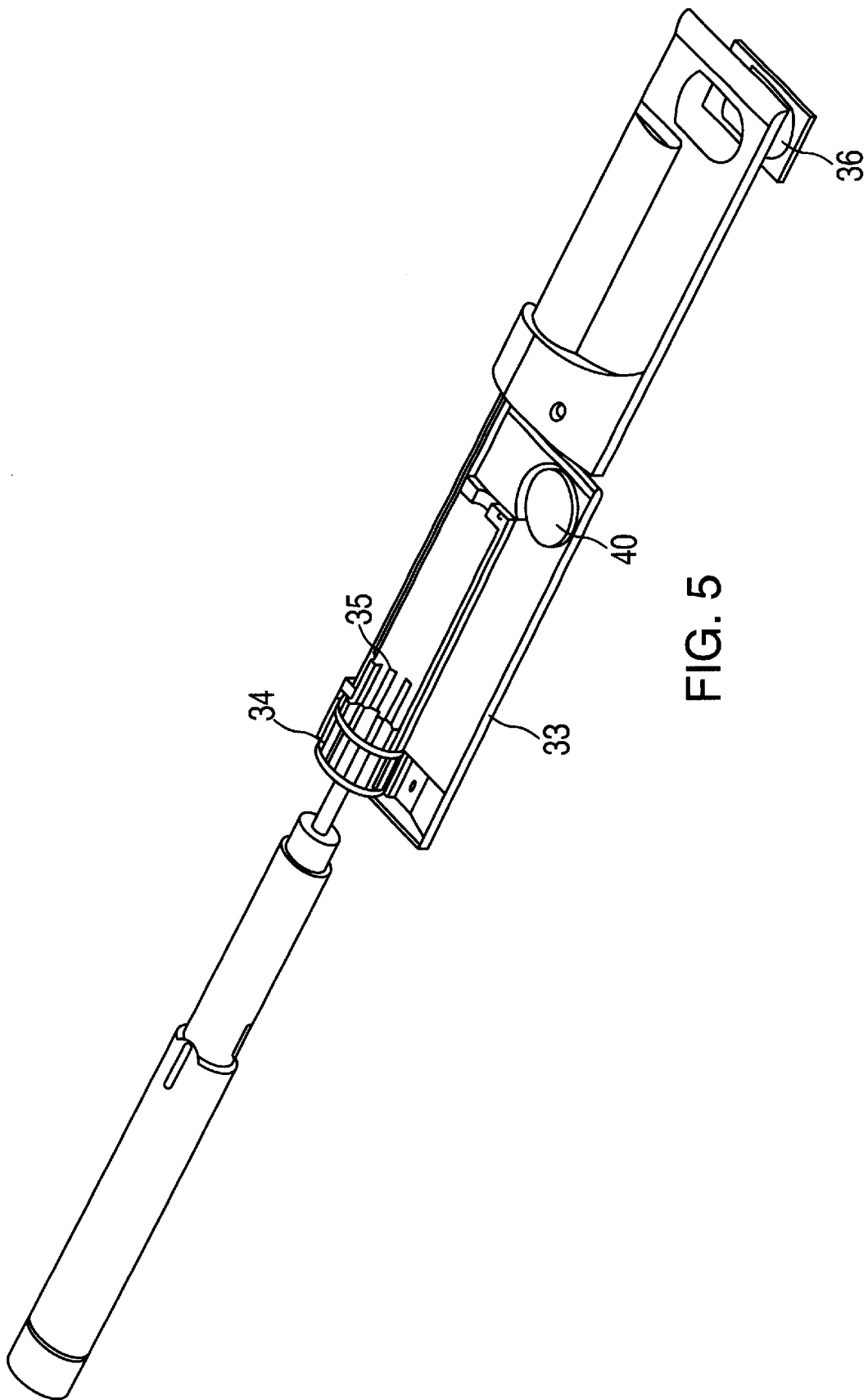

The invention is described in greater details below with reference to the accompanying drawings, in which FIG. 1 is a side view of a known injection pen which can be used in combination with the apparatus according to the invention, FIG. 2 is an axial sectional view of the unit shown in FIG. 1, FIG. 3 shows an embodiment of the invention and the injection pen shown in FIG. 1 and 2, FIG. 4 shows an apparatus according to the invention coupled with the injection pen shown in FIG. 1, FIG. 5 shows an exploded view of FIG. 3, FIG. 6 shows an internal view of an embodiment according to the invention coupled with the injection pen, cf. FIG. 4, FIG. 7 shows another embodiment for cooperating with add-on's, FIG. 8 schematically shows a further embodiment, and FIG. 9 shows a section through the embodiment shown in FIG. 8.

The injection pen shown in FIGS. 1 and 2 corresponds to the dosage unit known from EP 327 910. This dosage unit will therefore not be described in details below, but only to an extent necessary to understand how it works in principle with a preferred embodiment of the invention.

The dosage unit comprises a casing 1 for a cartridge 2 containing a liquid. The cartridge 2 comprises a piston 4 pressing the liquid out through a needle which must initially be mounted on a cup-shaped cap 6.

At the end opposite the cap 6, the dosage unit comprises a piston rod 8 driving the piston 4 in the cartridge 2. The piston rod 8 comprises a rail 9 provided with transverse barbs 10 being serrated when seen as a longitudinal sectional view thereof. These barbs co-operate with a pair of pawls 11 integral with the casing 1 and are provided with barbs for co-operating with said barbs 10 on the piston rod 8. Thereby a displacement of the piston rod 8 is allowed only towards the piston 4 of the cartridge.

Further the piston rod 8 is arranged relative to the casing 1 so that the piston rod 8 is prevented from rotating relative to the casing 1 whereas axial displacement is allowed.

The piston rod 8 is movable within an adjustment sleeve 18 having nut means 13 for co-operating with threaded portions on the piston rod 8, said thread being not visible in the drawing, since it exists only along the longitudinal top side (facing the viewer) of the rail 9 together with corresponding threaded protrusions diametrically opposite thereto. These rows of threaded protrusions are freely movable within the space 19 inside the adjustment sleeve 18 but when co-operating with the nut means 13, the adjustment sleeve 18 can be axially displaced when rotating the casing 1 in relation to an outer sleeve 20 since the adjustment sleeve 18 and the outer sleeve 20 are prevented from mutual rotational movement. Further details of these features can be ascertained from EP 327 910.

The dosage unit further comprises a removable cap 25 that protects the needle when mounted on the end cap 6. The removable cap 25 is of such axial extent that when mounted, its free rim 26 is situated adjacent the outer sleeve 20. Axial recesses or grooves are provided close to the free rim 26 of the cap 25, said recesses being situated with the same mutually angular distance along the inner side of the cap. These recesses are indicated by the reference numerals 27 and 28, and receive correspondingly shaped protruding projections 29,30, respectively, on the outer side of the casing 1.

It will now be explained how a pre-adjustment operation is performed by means of the known injection pen shown in FIGS. 1 and 2. When seizing the removable cap 25 and the outer sleeve 20, respectively, with one's fingers and turning these parts relative to each other, the adjustment sleeve 18 will be moved outwards (left in FIG. 2) and reveal a circumferential scale (see FIG. 4) which can be read relative to the end rim of the outer sleeve 20. This will be performed because the outer sleeve 20 and the removable cap 25 are coupled to the nut means 13 and threaded projections, respectively, as described above.

When the dosage is pre-adjusted, the corresponding amount of pharmaceutical can be pressed out by pressing the piston rod back to a position where the nut means 13 abut on the casing 1.

The problem for visually impaired patients may be that the numbers on the removable cap 25 and on the adjustment sleeve 18 (see FIG. 4) are relatively small. Also it may for some people be difficult to align the scale of the adjustment sleeve 18 relative to the rim of the outer sleeve 20, and such a failure is serious since this scale is calibrated into intervals of ten.

These and other problems are avoided by means of the invention, a preferred embodiment of which will now be described.

Referring now to FIG. 3, an embodiment 31 of the invention is shown in axial distance from the dosage unit or injection pen shown in FIGS. 1 and 2. The injection pen shown in FIG. 3 is further provided with a protection cap 32 surrounding the needle. The embodiment in FIG. 3 comprises a housing 33 with a window for an electronic display 36.

In use the injection pen is fully inserted into the apparatus as shown in FIG. 4 whereby the protrusions 29, 30 on the casing 1 and the projection 37 on the outer sleeve mesh with corresponding grooves in the apparatus 31 as explained below. The advantage of the invention is also illustrated on FIG. 4, cf. the scale shown on the adjustment sleeve 18 corresponding to a pre-adjustment of the dosage unit for delivering a dosage of 35 insulin units. It would be appreciated that the digits on the electronic display are more legible in relation to the small indications. on the adjustment sleeve. Also, misalignment of this scale in relation to the rim of the outer sleeve might occur. This is obviated according to the invention by the great digits on the display.

In FIG. 5 the apparatus is shown in its dismounted state whereby the free-running wheel 34 becomes visible. This wheel has a number of first engagement members in the form of axial slots or grooves for meshing with the projection 37. The housing 33 also has a number of second engagement members, fixed relative to the housing 33, in the form of axial grooves or slots as can be seen in FIG. 5 for receiving the projections 29,30. It will now be understood that when the injection pen has been fully inserted into the apparatus according to the invention, revolving of the apparatus 31 in relation to the outer sleeve 20 will perform two functions. First, since the casing 1 is fixed relative to the apparatus 31 against rotational movement, the injection pen will be pre-adjusted as explained above and second, the wheel 34 will be turned relative to the casing 33.

FIG. 6 shows other necessary components mounted in the casing 33. A detector means 12 is shown which is preferably an electrical transducer for co-operating with the wheel 34 for providing electrical signals representing the amount of rotation of the wheel 34 in relation to the casing 33. Preferably the signals represent a number of angular steps since it is preferred that the wheel 34 works with a ratchet in the casing whereby the user also has an audible response from the apparatus.

The signals representing the pre-adjusted dosage from the transducer 12 are transmitted to an electronic unit 38 which comprises electronic means at least for displaying on the display unit 36 an indication of the pre-selected dosage. Preferably a microswitch 39 is used for turning the electronics on and off, said switch being mounted so that the apparatus will not be switched on until the projections 29,30,37 mesh correctly with the corresponding grooves in the apparatus. Reference number 40 represents a bed for a battery.

It is an extremely expedient feature of the apparatus according to the invention that it can be used together with an injection pen already on the market. The adjustment obtained by turning the pen cap and outer sleeve relative to each other can also be obtained and detected by means of the apparatus, e.g. the electrical transducer 12, and the electronic unit 38 can be extended to comprise a computer with a memory, a preloaded program, and timer means so that almost any information about the previous, the actual, and the future dosage given by means of the injector pen can be stored, calculated on, and displayed.

E.g. clock means can be programmed to give an alarm after a preselected elapse of time and the memory can contain information about the amount of dosage given at a preselected time. Programming can be obtained by rotating the wheel 34, by means of the dosage unit, or by means of a programming dummy, but preferably the apparatus can be connected to different add-on's for a more convenient communication with other information systems.

Another embodiment of the apparatus according to the invention is shown on FIG. 7A arranged for communication with ad-on components, i.e. a sound module on FIG. 7B or a PC-link module 45 on FIG. 7C.

The embodiment of FIG. 7A has a greater electronic display 41 for showing more information than provided for with the display 36 on the first embodiment. The embodiment of FIG. 7A has connection means for cooperating with information transfer means 42,43 on the add-on's, i.e. the sound module 44 on FIG. 7B. On FIG. 7C the add-on is serving as a PC-link 45 for transferring information between the apparatus according to the invention and a PC installation, blood sugar measurement devices, or other equipment typically operated by doctors or the like. Thereby i.e. a whole pharmaceutical treatment can be loaded into the memory of the electronic unit 38 and information can be shown and alarms can be given to the patient ensuring that the prescribed pharmaceutical treatment is followed.

The apparatus according to the invention can in the most simple embodiment enhance the user's correct handling, especially when speaking about visually impaired users, but also people having no problems with the injection pen already on the market will ascertain many new advantages and one does not need to buy a quite new complete and more expensive equipment since the apparatus according to the invention can be used together with prior injection units, i.e. of the type above.

Till now the invention has been described in connection with an open-ended dosage unit which has been inserted in the apparatus. It will be realised from FIGS. 1 and 2 that well-known insulin pens normally also comprise a removable cap (25 in FIG. 1), and in the following an embodiment will be described which is arranged for receiving both the insulin pen and its corresponding cap.

In FIG. 8 the latter embodiment is shown where 46 represents the apparatus according to the invention while 20 corresponds to 20 in FIG. 1. FIG. 8 will not be explained further, but it should be mentioned that a rather big display 48 can be placed within the field marked 47.

FIG. 9 shows a section A-A from FIG. 8 which shows an insulin pen of a well-known type where the outer sleeve 20 and the cap 25 are shown in bold line.

The apparatus 46 comprises a display 48, an electronic circuit board 49, a battery 50, a micro processor 51, a cap switch 52 and a pen switch 53.

The cap 25 has a cap clip 54 which is received in a groove (not shown) in the apparatus so that the cap clip is prevented from rotation relative to the apparatus 46.

Correct insertion of the pen in the apparatus will be realised by the cap switch 52. The cap 25 will be retained in the apparatus 46 by means of friction and elastic elements in a well known manner.

The function can be easily understood when comparing with FIG. 3 and 5. In FIGS. 3 and 5 the protrusion 29 is received in one of the grooves 35, but in the embodiment shown in FIGS. 8 and 9 the protrusion 29 will be received in a corresponding groove in the cap. Since the cap itself is prevented from rotation in the apparatus 46, then the insulin pen can be adjusted by turning the outer sleeve 20 in relation to the apparatus 46. Thereby the protrusion 37 in FIG. 3 will engage a wheel 55 corresponding to the wheel 34 in FIG. 5, the wheel 55 having on its outer periphery a number of studs for cooperating with for example three electrical contacts in parallel whereby the safe detection of the setting of the pen can be enhanced. Especially when turning the parts quickly relative to each other, the latter embodiment will be more reliable than the previous embodiment.

After an insulin dose has been injected some insulin may leak from the needle. If this insulin runs into the apparatus 46 it can damage the electronic parts, and further there is a risk of bad smell due to the preservative substances in the insulin. These drawbacks are eliminated because the cap 25 is received in the apparatus and prevents the insulin from causing damage. Also if a failure should arise in the apparatus 46 e.g. low battery, then the well-known insulin pen comprising the outer sleeve 20 and the cap 25 can be disconnected from the apparatus 46 by moving the insulin pen to the left in FIG. 9. Thereafter, the pen can be adjusted in a well-known manner.

What is claimed is:

1. An apparatus for use in setting the dose of a syringe of the type having two parts which are rotatable relative to one another to set the size of a dose, said apparatus comprising:

a housing including a receiving portion for detachably securing a syringe of the foregoing type while setting a dose, wherein such syringe may thereafter be released from such receiving portion in order to inject the set dose, a first engagement member coupled to the housing and positioned to engage one of the two parts of such syringe when the syringe is secured in the receiving portion, a second engagement member coupled to the housing and positioned to engage the other of the two parts of such syringe when the syringe is secured in the receiving portion, wherein at least one of the engagement members is moveable relative to the housing such that the engagement members are movable relative to one another responsive to relative rotatation of the two parts of such syringe;

a detector means coupled to at least one of the engagement members for detecting relative movement of the engagement members; and an information providing means coupled to the detector means for providing information relating to the amount of relative movement of the engagement members.

2. An apparatus according to claim 1 for use with a syringe having opposite ends which are rotatable relative to one another to set a dose, wherein the first engagement member is secured to the housing to prevent rotation of one end of the syringe when such a syringe, which syringe is of the type is secured in the receiving portion, such that a dose may be set by rotating the opposite end of such syringe.

3. An apparatus according to claim 2 for use with a syringe, which syringe is of the type in which each of the two parts includes an engagable member, and wherein the engagement members of the housing are each positioned to engage one of the engagable members of such syringe when the syringe is secured in the receiving portion, wherein the second engagement member is coupled to the housing for rotation along with the opposite end of such syringe, and wherein the detector means detects rotation of the second engagement member relative to the housing.

4. An apparatus according to claim 3, wherein the detector means comprises a transducer for generating an electrical signal which represents a quantity set.

5. An apparatus according to claim 4, wherein the transducer comprises an encoder.

6. An apparatus according to claim 5, wherein the information means comprises a memory and programming unit.

7. An apparatus according to claim 4 wherein the transducer generates different electrical signals depending upon the direction of rotation of the second engagement member.

8. An apparatus according to claim 4, wherein the information means comprises a display unit, the display of which depends on the electrical signal.

9. An apparatus according to claim 1, wherein the detector means comprise a transducer for generating an electrical signal which represents a quantity set.

10. An apparatus according to claim 9, wherein the apparatus further comprises a sound module.

11. An apparatus according to claim 10, wherein the sound module is a separate, add-on element being operably connectable with the apparatus.

12. An apparatus according to claim 9, wherein the apparatus further comprises a PC-link module.

13. An apparatus according to claim 12, wherein the PC-link module is a separate, add-on element being operably connectable with the apparatus.

14. An apparatus according to claim 9, wherein the information means comprises clock and timer means.

15. An apparatus according to claim 1, wherein the apparatus is for use with a syringe having a removable cap covering one end of the syringe, which cap comprises one of the two mutually rotatable parts of such syringe, and wherein the first engagement member is positioned to engage such cap when the syringe is secured in the receiving portion.

16. An apparatus according to claim 15 for use with a syringe, which syringe is of the type having opposite ends which are rotatable relative to one another to set a dose, the cap comprising one such end, wherein the first engagement member is secured to the housing to prevent rotation of the cap of such syringe relative to the housing when a syringe is secured in the receiving portion, such that a dose may be set by rotating the opposite end of such syringe.

17. An apparatus according to claim 16 for use with a syringe in which the cap includes an engagable element, wherein the first engagement member is positioned to engage the engagable element of such a cap when the syringe is secured relative to the receiving portion.

18. An apparatus according to claim 1, wherein the detector means is coupled to the information providing means to provide an indication of a set dosage quantity.

19. The combination of a syringe having two mutually rotatable parts for setting a dose, and an apparatus for use while setting a dose, wherein said apparatus comprises:

a housing including a receiving portion in which the syringe is detachably secured for setting a dose, wherein the syringe may be released from such receiving portion after setting the dose in order to inject the set dose, a first engagement member coupled to the housing and positioned to engage one of the two parts of the syringe, a second engagement member coupled to the housing and positioned to engage the other of the two parts of such syringe, wherein at least one of the engagement members is moveable relative to the housing such that the engagement members are movable relative to one another responsive to relative rotatation of the two parts of such syringe;

a detector means coupled to at least one of the engagement members for detecting relative movement of the engagement members; and an information providing means coupled to the detector means for providing information relating to relative movement of the engagement members.

20. The combination according to claim 19, wherein the syringe includes opposite ends which are rotatable relative to one another to set a dose, and wherein the first engagement member is positioned to prevent rotation of one end relative to the housing such that a dose may be set by rotating the opposite end of such syringe.

21. The combination according to claim 20, wherein each of the two parts of the syringe includes an engagable member, and wherein the engagement members of the housing are each positioned to engage one of the engagable members of the syringe, wherein the second engagement member is coupled to the housing for rotation along with the opposite end of the syringe, and wherein the detector means detects rotation of the second engagement member relative to the housing.

22. The combination according to claim 21, wherein the syringe has a removable cap covering one end which comprises one of the two mutally rotatable parts of such syringe and contains an engagable member, and wherein the first engagement member is positioned to engage the cap to prevent rotation thereof.

* * * * *